(12) United States Patent
Rajendran

(10) Patent No.: US 8,258,346 B2
(45) Date of Patent: *Sep. 4, 2012

(54) SURFACE MODIFIED HEXAGONAL BORON NITRIDE PARTICLES

(75) Inventor: Govindasamy Paramasivam Rajendran, Garnet Valley, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 462 days.

This patent is subject to a terminal disclaimer.

(21) Appl. No.: 12/465,042

(22) Filed: May 13, 2009

(65) Prior Publication Data

US 2010/0292508 A1 Nov. 18, 2010

(51) Int. Cl.
*C07F 5/02* (2006.01)
*B32B 27/14* (2006.01)
(52) U.S. Cl. ................................ 568/1; 428/195.1
(58) Field of Classification Search .... 568/1; 428/195.1
See application file for complete search history.

(56) References Cited

U.S. PATENT DOCUMENTS

| | | | |
|---|---|---|---|
| 4,670,325 A | 6/1987 | Bakos et al. | |
| 5,298,331 A | 3/1994 | Kanakarajan et al. | |
| 5,681,883 A | 10/1997 | Hill et al. | |
| 6,143,819 A | 11/2000 | Nakanishi | |
| 6,160,042 A | 12/2000 | Ishida | |
| 6,162,849 A | 12/2000 | Zhuo et al. | |
| 6,652,822 B2 | 11/2003 | Phillips et al. | |
| 7,026,436 B2 | 4/2006 | Kanakarajan | |
| 7,189,774 B2 | 3/2007 | Clere | |
| 7,470,990 B2 | 12/2008 | Japp | |
| 7,527,859 B2 | 5/2009 | Zhong et al. | |
| 7,658,988 B2 | 2/2010 | Lin et al. | |
| 7,829,188 B2 | 11/2010 | Lin | |
| 2002/0018885 A1 | 2/2002 | Takakashi et al. | |
| 2002/0086168 A1 | 7/2002 | Sadvary et al. | |
| 2006/0127422 A1 | 6/2006 | Lodyga et al. | |
| 2006/0127686 A1 | 6/2006 | Meloni | |
| 2007/0041918 A1 | 2/2007 | Meneghetti et al. | |
| 2007/0054122 A1 | 3/2007 | Paisner et al. | |
| 2007/0205706 A1 | 9/2007 | Yamada et al. | |
| 2007/0241303 A1 | 10/2007 | Zhong et al. | |
| 2007/0259211 A1 | 11/2007 | Wang | |
| 2008/0076856 A1 | 3/2008 | Zhong et al. | |
| 2008/0093422 A1 | 4/2008 | Kodas | |
| 2009/0304922 A1 | 12/2009 | Boussaad | |
| 2009/0305043 A1 | 12/2009 | Boussaad | |
| 2010/0055365 A1 | 3/2010 | Nakajima et al. | |
| 2010/0159244 A1 | 6/2010 | Boussaad | |
| 2010/0291365 A1 | 11/2010 | Lin et al. | |
| 2010/0291371 A1 | 11/2010 | Kanakarajan et al. | |
| 2010/0292508 A1 | 11/2010 | Rajendran | |

FOREIGN PATENT DOCUMENTS

| | | |
|---|---|---|
| EP | 0794227 B1 | 10/2002 |
| GB | 1536320 | 12/1978 |
| JP | 07-215705 | 8/1995 |
| WO | 2008140583 A2 | 11/2008 |

OTHER PUBLICATIONS

Mevellac et al., Grafting Polymers on Surfaces: A New Powerful and Versatile Diazonium Salt-Based One-Step Process in Aqueous Media, Chem. Mater., vol. 19 (2007), pp. 6323-6330.
Grieve et al., 151. Reactivity of Carbenes and Related Compounds Towards Molecular Nitrogent, Helvetica Chimica Acta, vol. 68 (1985), pp. 1427-1443.
International Search Report, PCT/US2010/034459 filed May 12, 2010.
International Search Report, PCT/US2010/034462 filed Dec. 29, 2010.
T. Ikuno, Amine-Functionalized Boron Nitride Nanotubes, Solid State Communications, 2007, vol. 142, pp. 643-646.
Dmitri Golberg, Boron Nitride Nanotubes, Advanced Materials, 2007, vol. 19, pp. 2413-2432.
Y.L. Zhou Surface Functionalization of Cubic Boron Nitride Films for Biological Sensing Applications, Applied Physics Letters, 2008, vol. 92, 163105-1-163105-3.
Wu et al., Chemical Functionalization of Boron-Nitride Nanotubes With NH3 and Amino Functional Groups, J.Am.Chem. Soc., 2006, 128, 12001-12006.
Mitchell Huang and Hatsuo Ishida, Surface Study of Hexagonal Boron Nitride Powder by Diffuse Reflectance Fourier Transform Infrared spectroscopy, Surf. Interface Anal, 2005, 37, 621-627.

*Primary Examiner* — Jafar Parsa

(57) ABSTRACT

Provided is a composition comprising hexagonal boron nitride particles having a surface and a substituted phenyl radical bonded to the surface, the substituted phenyl radical being represented by the structure:

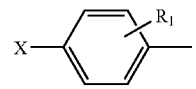

where X is a radical selected from $NH_2$—, HO—, $R_2OC(O)$—, $R_2C(O)O$—, $HSO_3$—, $NH_2CO$—, halogens, alkyl or aryl, including substituted aryl; where $R_1$ is hydrogen, alkyl or alkoxy, and $R_2$ is hydrogen, alkyl or aryl, including substituted aryl. A process for preparing the composition is also provided.

10 Claims, 3 Drawing Sheets

SURFACE MODIFIED HEXAGONAL BORON NITRIDE PARTICLES

RELATED CASES

This application is related to co-owned U.S. patent application Ser. Nos. 12/465,042, 12/465,090, and 12/465,128 respectively designated as CL4658USNA, CL4659USNA, and CL4660USNA filed on the same day as the present application.

FIELD OF THE INVENTION

The present invention deals with the preparation of surface modified hexagonal boron nitride particles that are suitable for incorporation into polymers at high concentrations.

BACKGROUND

Meneghetti et al. U.S. 2007/0041918, discloses hexagonal boron nitride treated with a zirconate and employed up to 75% by weight in polymers to prepare samples of improved thermal conductivity.

Sainsbury et al., WO 2008/140583, discloses amine (NH2) modified BN nanotubes by exposure to $NH_3$ plasma. Incorporation into a polymer is mentioned.

Ishida, U.S. Pat. No. 6,160,042, discloses boron nitride surface-treated with 1,4 phenylene diisocyanate incorporated into epoxy resins.

Mevellec et al., Chem. Mater. 2007, 19, 6323-6330, discloses that redox activation of aryl diazonium salts with iron powder in the presence of vinylic monomers in aqueous solution leads to very homogeneous thin polymer films strongly grafted on various surfaces such as (Au, Zn, Ti, stainless steel), glasses, carbon (nanotubes) or PTFE.

Epoxies and polyimides, are commonly used as components in printed circuit boards. As the density of elements in electronic circuits increases, heat management is an ever increasing problem. Incorporation into polymers of 50 volume % and more of hexagonal boron nitride (hBN) particles imparts enhanced thermal conductivity without compromising electrical insulation. In general, surface treatment of the BN particles is required in order to achieve adequate dispersion and moldability.

However, even with surface treatment, the high loading of hBN particles required for improved thermal conductivity in a given polymer causes a large increase in viscosity with concomitant degradation in processibility. This is especially a problem in producing substrate films for flexible printed circuit boards.

SUMMARY OF THE INVENTION

The invention provides a composition comprising hexagonal boron nitride particles having a surface and a substituted phenyl radical bonded to the surface, the substituted phenyl radical being represented by the structure:

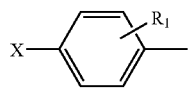

where X is a radical selected from $NH_2$—, HO—, $R^2OC(O)$—, $R^2C(O)O$—, $HSO_3$—, $NH_2CO$—, halogens, alkyl and aryl, including substituted aryl; $R^1$ is hydrogen, alkyl or alkoxy, and $R^2$ is hydrogen, alkyl or aryl, including substituted aryl.

Further provided in the present invention is a process comprising reacting particles of hexagonal boron nitride with a substituted phenyl diazonium chloride in an alcohol/water solution in the presence of metallic iron and HCl, and recovering the reaction product therefrom; wherein the alcohol/water solution has a water concentration of at least 50% by volume; and wherein the substituted phenyl diazonium chloride is represented by the formula

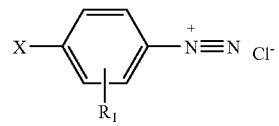

where X is selected from NH2-, HO—, $R^2OC(O)$—, HSO3-, NH2CO—, halogens, alkyl and aryl, including substituted aryl; $R^1$ is alkyl or alkoxy, and $R^2$ is hydrogen, alkyl or aryl, including substituted aryl.

DETAILED DESCRIPTION

Figure 1:
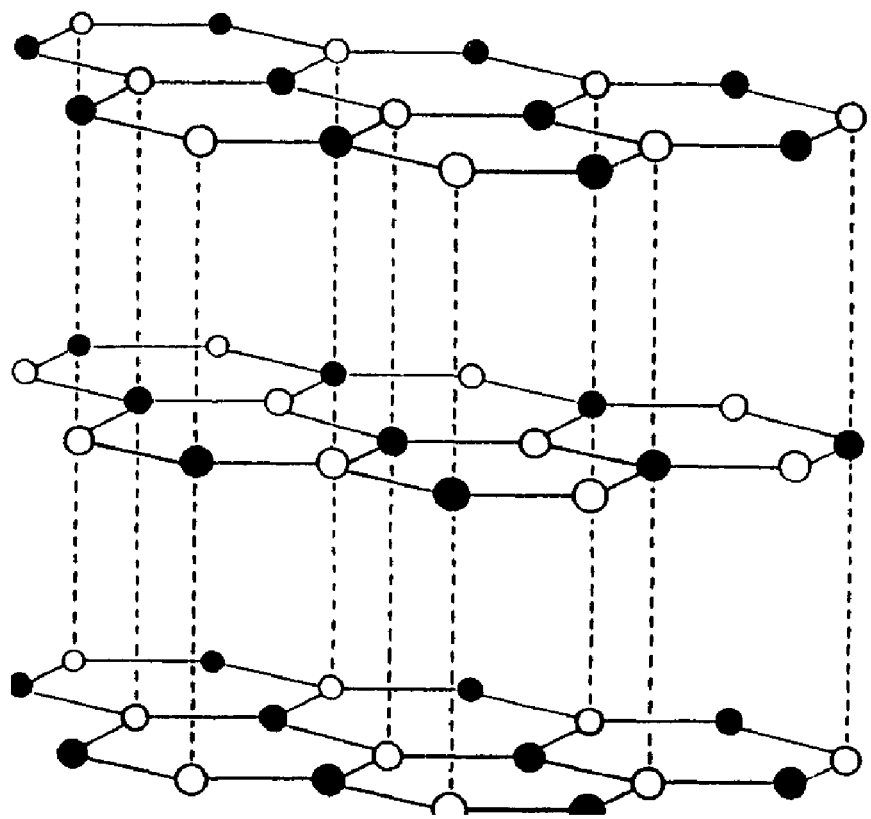
FIG. 1 is a schematic representation of the structure of a hexagonal boron nitride particle.

In the present invention a novel treatment for hBN is provided that produces a new chemical species on the surface of hBN particles, making them highly compatible with thermoset polymers such as epoxies and polyimides, and provides tough, flexible substrates for flexible printed circuit boards.

Whenever a range of values is provided herein, the range is intended to encompass the endpoints of the range unless it is specifically stated to be otherwise.

In one embodiment, the polymer is a thermoset polymer, or the uncured (or uncross-linked) thermosettable polymeric precursor corresponding thereto. When the precursor polymer is subject to elevated temperature it undergoes a cross-linking reaction (or curing reaction) or imidization that converts a flowable and/or formable polymer into a non-flowable, non-formable polymer. Suitable thermoset polymers include but are not limited to polyimides and cured epoxy resins. Suitable thermosettable precursor polymers include polyamic acids and epoxide polymers. The curing process may or may not involve the addition of a cross-linking agent. Conversion of some polymers requires addition of a cross-linking agent.

The term "flowable" refers to a viscous mass which is displaced upon the application of a shear force. The term "formable" refers to a viscous mass which can be formed into a shaped article and will hold the shape for sufficient time that it can be set in that shape, either by cooling, curing, or imidization. In general, all formable masses are flowable, but not all flowable masses are formable. Formable masses are generally of higher viscosity than non-formable but flowable masses.

Polyimides are uncrosslinked thermoplastic polymers which generally decompose before they melt. Polyimides do not exhibit flow at temperatures as high as 500° C. However, as used herein, the term "thermoset polymer" encompasses polyimides, and the term "thermosettable polymer" encompasses polyamic acids.

The present invention provides films having a thickness less than 500 μm. Films are generally prepared, for example, by melt casting or solution casting onto a release surface. In one embodiment, the films have a thickness in the range of 10 to 100 μm. In a further embodiment, the films have a thickness in the range of 15 to 80 μm. Films that are too thin may exhibit insufficient toughness for use as substrates for printed circuit boards. Films that are too thick may exhibit insufficient flexibility to be useful as substrates for flexible printed circuit boards.

Viscosity as described herein is determined at room temperature according to ASTM D 2196-05, using a Brookefield viscometer, Model DV-II+, spindle #28.

In one aspect, the present invention provides a composition (herein designated SMhBN) comprising hexagonal boron nitride particles having a surface and a substituted phenyl radical bonded to the surface, the substituted phenyl radical being represented by the structure:

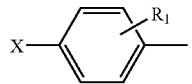

where X is a radical selected from $NH_2$—, HO—, $R^2OC(O)$—, $R^2C(O)O$—, $HSO_3$—, $NH_2CO$—, halogens, alkyl and aryl, including substituted aryl; where $R^1$ is hydrogen, alkyl or alkoxy, and $R^2$ is hydrogen, alkyl or aryl, including substituted aryl.

In one embodiment, $R^1$ is hydrogen. In another embodiment, X is $NH_2$— or HO—. In another embodiment, X is $NH_2$—. In another embodiment, X is HO—. The substituted phenyl radical is bonded to the surface of the hBN.

Hexagonal boron nitride particles are known to be represented by the structure shown in FIG. 1, consisting of multiple stacked, registered platelets, offering a high surface area for reaction. The white and black alternating circles represent nitrogen and boron atoms arranged in hexagonal lattices. There are no particular size limitations for the hBN particles employed herein. Typical commercially available hBN particles fall in size range of about 0.7 micrometer, about 10 to 12 μm, and about 14 to 15 μm. As the particle size grows smaller, the particle is harder to disperse. On the other hand, as the particle size grows larger, the composite film may exhibit undesirable surface roughness.

In one embodiment, the SMhBN has a concentration of the substituted phenyl radical in the range 0.1 to 4.0% by weight on the basis of SMhBN.

In another aspect the invention provides a process for producing the SMhBN, comprising reacting particles of hexagonal boron nitride with a substituted phenyl diazonium chloride in an alcohol/water solution in the presence of metallic iron and dilute HCl, and recovering the reaction product therefrom; wherein the alcohol/water solution has a water concentration of at least 50% by volume; and wherein the substituted phenyl diazonium chloride is represented by the formula

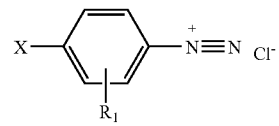

where X is selected from $NH_2$—, HO—, $R^2OC(O)$—, $HSO_3$—, $NH_2CO$—, halogens, alkyl and aryl, including substituted aryl; $R^1$ is alkyl or alkoxy, and $R^2$ is hydrogen, alkyl or aryl, including substituted aryl. In one embodiment, $R^1$ is hydrogen. In another embodiment, X is $NH_2$— or HO—. In another embodiment, X is $NH_2$—. In another embodiment, X is HO—.

In one embodiment, the water/alcohol solution is at least 80% by volume water.

Suitable substituted phenyl diazonium chlorides may be prepared using known methods. For example, preparation of 4-amino-benzene diazonium chloride is described in United Kingdom Patent GB1536320. preparation of 4-hydroxy-benzene diazonium chloride is described in Grieve et al., Helvetica Chimica Acta; English; 68; 1985; 1427-1443, and preparation of 4-carboxy-benzene diazonium chloride is described in Weedon; American Chemical Journal; 33; 1905; 417.

In one embodiment, the molar ratio of the substituted benzene diazonium chloride to hBN in the reaction mixture is in the range of 0.005:1 to 0.1 to 1. In one embodiment, iron is added in molar excess over the amount of substituted phenyl diazonium chloride. In a further embodiment, iron is added as a powder. In a still further embodiment, the iron powder is less than-1-2 mm in at least one dimension (10 mesh).

The amount of modifier residing on the surface of the hBN depends upon the surface area of the hBN and the reactivity of the phenyl radical. A phenyl radical containing an electron donating group (such as amine or alkyl) is more reactive, while a phenyl radical containing an electron withdrawing group (such as COOH or OH) is less reactive. The effect of hBN surface area on the amount of uptake of a given phenyl radical is shown in Table 1:

TABLE 1

| Particle size (hBN) | surface area (m2/g) | Phenyl radical concentration |
| --- | --- | --- |
| NX1 (0.7 um) | 20 | 1.93% |
| PT120 (12-13 um) | 2.0 | 0.42% |

It has been found that the reaction rate is governed by the reactivity and half life of the radical, and the susceptibility of the substrate to undergo reaction. The lower reactivity hydroxyphenyl radical results a smaller amount of substituted phenyl radical surface modification of hBN than does the higher reactivity aminophenyl radical when the starting materials are in the same ratio.

In one embodiment of the process, iron is present in excess. The iron is thought to provide a surface upon which the reduction of the diazonium salt to the radical takes place The reduction reaction may proceed to a higher degree if iron is present in excess. An excess of iron insures that all the diazonium salt is reduced, avoiding the explosion hazard associated with having residual diazonium salt.

Dilute acid reduces the rate of reaction of the diazonium salt and thereby reduces explosion hazard. It has been found that for the processes disclosed herein dilute HCl (in one embodiment, 0.1-1.0 M, in a further embodiment 0.3 to 0.7 M) is satisfactory. Because of the relative stability of the diazonium chloride, use of HCl is desirable to avoid possible explosion.

In one embodiment the reaction is conducted at room temperature.

In one embodiment of a batch process, an aqueous solution of substituted benzene diazonium chloride is mixed with a dispersion of hBN in water/alcohol mixture. The iron particles are then added to the mixture and stirred for several minutes, followed by addition of HCl, which is followed by further stirring for about 30 minutes. The concentration of HCl in the reaction mixture does not exceed 0.1 M.

In one embodiment, the iron particles are removed with a magnet, and the SMhBN is isolated by filtration and drying.

Viscosity suitable for handling and mixing the reaction mixture is obtained by combining alcohol with water. Suitable alcohols include, but are not limited to, the $C_1$ to $C_6$ alkyl alcohols, including methanol, ethanol, and propanol. Concentrations of alcohol greater than 50% by volume have little additional effect on viscosity, but represent a safety hazard. The diazonium chloride compositions employed herein are inherently unstable, particularly when not in solution. Should a destabilizing event occur, the presence of a flammable liquid such as an alcohol would add undesirable fuel to the fire.

In one embodiment a 50/50 mixture by volume of water and alcohol is employed as the solvent for the for the surface modification reaction. In a further embodiment, a mixture of 80 vol-% water and 20 vol-% methanol is employed.

In another embodiment, the SMhBN is combined with a polymer to prepare a polymer composition comprising a polymer and a plurality of surface-modified hexagonal boron nitride particles dispersed therewithin, the surface modified hexagonal boron nitride particle comprising a hexagonal boron nitride particle having a surface and a substituted phenyl radical bonded to the surface, the substituted phenyl radical being represented by the structure:

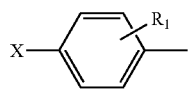

where X is a radical selected from $NH_2$—, HO—, $R^2OC(O)$—, $R^2C(O)O$—, $HSO_3$—, $NH_2CO$—, halogens, alkyl and aryl, including substituted aryl; $R^1$ is alkyl or alkoxy, and $R^2$ is hydrogen, alkyl or aryl, including substituted aryl.

In one embodiment, $R^1$ is hydrogen. In another embodiment, X is $NH_2$— or HO—. In another embodiment, X is $NH_2$—. In another embodiment, X is HO—.

In one embodiment, the polymer comprises polyamic acid. In a further embodiment, the polyamic acid is in solution. In another embodiment, the polymer is a polyimide. In another embodiment, the polymer is an epoxy-containing polymer either in the liquid state or in solution. In another embodiment, the polymer is a cured epoxy resin.

Polyimide chemistry is very well-known in the art; see for example the article in the *Encyclopedia of Polymer Science and Technology* by Bryant, DOI 10.1002/0471440264.pst272.pub2. Condensation polyimides are normally prepared by imidization of a corresponding polyamic acid. Suitable polyamic acid compositions include but are not limited to the polymers prepared by the reaction of equimolar amounts of diamines and tetracarboxylic dianhydrides (or the dianhydride's acid ester or the acid halide ester derivative) in suitable solvents. In one embodiment, the anhydride moiety is selected from the group consisting of pyromellitic dianhydride (PMDA), 4,4-oxydiphthalic dianhydride (ODPA), 3,3',4,4'-benzophenonetetracarboxylic dianhydride (BTDA), 3,3',4,4'-biphenyltetracarboxylic dianhydride (BPDA), 2,2'-bis(3,4-dicarboxyphenyl) 1,1,1,3,3,3,-hexafluoropropane dianhydride (FDA), and 2,3,6,7-naphthalene tetracarboxylic dianhydrides.

Suitable diamines include 1,4-phenylene diamine (PPD), 1,3-phenylene diamine (MPD), 4,4'-diaminodiphenyl ether (4,4'-ODA), 3,4'-diaminodiphenyl ether (3,4'-ODA), 1,3-bis-(4-aminophenoxy)benzene (APB-134), 1,3-bis-(3-aminophenoxy)benzene (APB-133), 2,2'-bis-(4-aminophenyl)-1,1,1,3,3,3-hexafluoropropane (6F diamine), and bis[4-(4-aminophenoxy)phenyl]ether (BAPE).

The polyamic acid formed may be either a homopolymer, or random copolymer if more than one diamine and/or dianhydrides are used for the polymerization. Segmented copolymers can be formed by polymerizing initially with an excess of a first diamine or first dianhydrides and then adding different dianhydrides or diamines respectively.

Polyamic acids, by virtue of their solubility in a variety of solvents, are more highly processable than the corresponding polyimide. It is common practice in the art to perform any mixing and forming operations on the polyamic acid composition followed by imidization. Polyimides are well-known to be highly inert to solvents and elevated temperatures.

Epoxy chemistry is very well-known in the art; see for example the article in the *Encyclopedia of Polymer Science and Technology* by Pham and Marks, DOI 10.1002/0471440264.pst119. "Epoxy resins" is the term of art employed to refer to a cured epoxy. An uncured epoxy has a cyclic epoxide group along the polymer chain. A cured epoxy is one in which a preponderance of the cyclic epoxide groups have undergone reaction with a curing agent (also known as a cross-linking agent) to form cross-links among polymer chains thereby forming a rigid, substantially inert 3-D network of polymer chains. Suitable uncured epoxy compositions comprise one or more multifunctional or difunctional epoxy resins, an epoxy curing agent, a toughener and a curing accelerator.

Suitable multifunctional epoxy resins include but are not limited to phenol-novolac epoxy, cresol-novolac epoxy, tetraglycidyl ether of diaminodiphenylmethane, triglycidyl tris (hydroxylphenyl)methane, trigylcidyl ether of p-aminophenol, naphthalene epoxy resin, the trigylcidyl derivative of cyanuric acid, the epoxy derivative of biphenol. Suitable difunctional epoxy resins include but are not limited to glycidyl ethers of bisphenol A, bisphenol F and bisphenol S, and reactive diluents such as aliphatic epoxies.

Suitable curing agents for epoxies include but are not limited to amines, amides, anhydrides, polyamides, polyamine adducts, organic acids, phenols and phenolic resins. Phenolic curing agents are particularly preferred for their moderating effects on viscosity of the composition and moisture absorption, good electrical and high temperature mechanical properties. Suitable phenolic curing agents include bisphenol A, xylok type phenol resin, dicyclopentadiene type of phenol, terpene modified phenolic reisn, phenolic resin and polyvinylphenol.

In one embodiment, the epoxy composition also includes polymeric toughening agents having average molecular weight in the range 5000-100000, and being soluble in the the epoxy resin solution. Suitable polymeric tougheners include but are not limited to phenoxys, acrylics, polyamides, polycyanates, polyesters and polyphenylene ethers.

In a further embodiment, the epoxy composition also contains a curing accelerator. Suitable curing accelerators include but are not limited to amines, guanidine, imidazoles, triphenyl phosphine, triphenyl phosphonium tetrafluoroborate, or epoxy adducts thereof.

Uncured epoxies, by virtue of their inherent liquidity at room temperature or solubility in a variety of solvents are more highly processible than the corresponding cured epoxy. It is common practice in the art to perform any mixing and forming operations on the uncured epoxy composition followed by curing. Cured epoxy polymers are well-known to be highly inert to solvents and elevated temperatures.

In one embodiment, the polymer composition comprises 30-70% by weight of the SMhBN. In a further embodiment, the polymer composition comprises 40-65% by weight of the SMhBN. In one embodiment, the average equivalent spherical diameter of the SMhBN is in the range of 0.5 μm to 50 μm. In a further embodiment, the average equivalent spherical diameter of the SMhBN is in the range of 0.5 to 25 μm.

It is not necessary to break up agglomerated SMhBN. Usually the SMhBN does not agglomerate readily. PT620 is sold as agglomerated hBN by the vendor. In some embodiments, agglomerated SMhBN is preferred for improved thermal conductivity. Agglomerates of SMhBN can be soft or hard. Hard agglomerates form by surface modifying PT620 Agglomerates having sizes in the range 0.5-50 micrometer are suitable. In one embodiment, the SMhBN dispersed in the polymer can be characterized by a plurality of particle size distribution peaks characteristic of a so-called multi-modal particle size distribution.

Particles having a size of about 1/10 of the desired film thickness or less are desirable to make smooth-surfaced films having isotropically balanced mechanical and thermal properties. Increasing particle size introduces anisotropy and surface roughness.

In another aspect, the invention provides a process comprising combining a plurality of surface-modified hexagonal boron nitride particles with a polymer solution comprising a solvent, and, extracting the solvent, wherein the surface-modified hexagonal boron nitride particles comprise hexagonal boron nitride particles having a surface and a substituted phenyl radical bonded to the surface, the substituted phenyl radical being represented by the structure:

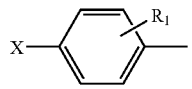

where X is a radical selected from $NH_2$—, HO—, $R^2OC(O)$—, $R^2C(O)O$—, $HSO_3$—, $NH_2CO$—, halogens, alkyl and aryl, including substituted aryl; $R^1$ is alkyl or alkoxy, and $R^2$ is hydrogen, alkyl or aryl, including substituted aryl.

In one embodiment, $R^1$ is hydrogen. In another embodiment, X is $NH_2$— or HO—. In another embodiment, X is $NH_2$—. In another embodiment, X is HO—.

In one embodiment, the process further comprises combining a dispersion of SMhBN in a first organic liquid, with a solution of a polymer in a second organic liquid, with the proviso that the first and second organic liquids are miscible, and are both solvents for the polymer.

When the polymer is a polyamic acid, suitable organic liquids include but are not limited to N,N'-dimethyl acetamide, N,N'-dimethyl formamide, N-methyl pyrrolidone, tetramethyl urea, dimethyl sulfoxide, and hexamethyl phosphoramid.

When the polymer is an epoxy resin, suitable organic liquids include but are not limited to acetone, methyl ethyl ketone, cyclohexanone, propylene glycol mono methyl ether acetate, carbitol, butyl carbitol, toluene, and xylene.

In one embodiment, the SMhBN is dispersed within the first organic liquid at a solids content in the range of 20 to 70% by weight. In a further embodiment, solids content is in the range of 30-40% by weight The dispersion is readily achieved by simple mixing using any mechanical stirrer.

In one embodiment, the first and second organic liquids are both dimethylacetamide (DMAc), and the concentration of SMhBN is 30-40%. In this embodiment, the dispersion viscosity is below 100 cp at room temperature. It has been found that viscosity below 100 cp is often insufficient to obtain homogeneous mixing of the dispersed SMhBN in the polymer solution. In a further embodiment, a masterbatch of 30-40% SMhBN in DMAc is prepared by adding about 5-20% by weight of polymer based upon the weight of the SMhBN. The presence of the polymer increases the viscosity above 100 cp, and allows good mutual dispersion of polymer and SMhBN, resulting in a masterbatch comprising a relative concentration of SMhBN/polymer in the range of 96/4 to 80/20. The masterbatch so produced can then be mixed with further polymer solution to produce the final desired concentration of SMhBN in the polymer, namely SMhBN in the range of 30-70% by weight on the basis of total solids, in one embodiment, 40-65% by weight of the total solids. In one embodiment, the polymer is polyamic acid. In an alternative embodiment, the polymer is uncured epoxy resin.

The polymeric dispersions are produced by high shear mixing. Suitable high shear mixers include but are not limited to homogenizers (available from Silverson Mechanics Inc, East Long Meadow, Mass.), blenders, ultrasonic agitators, or roller mills with grinding media. Suitable ranges for the viscosity of the dispersion, comprising organic liquid, SMhBN and polymer, for high shear mixing can be in the range of 100 to 2000 cp, preferably in a viscosity range of 200 to 1500 cp.

In one embodiment, the second organic liquid can be a liquid polymer, for example, a liquid epoxy resin having relatively low molecular weight and viscosity Liquid epoxy resins suitable for use in the process are made from bisphenol A, bisphenol F, epoxy modified liquid rubber, epoxy resins derived from polyhydric alcohols such as ethylene glycol, propylene glycol, neopentyl glycol and the like. Reactive diluents such as allylglycidyl ether, glycidyl methacrylate, and allylphenyl glycidyl ether can also be used to improve dispersion of the SMhBN. It has been found that the viscosity suitable for high shear mixture is in the range 200 to 1500 cp. Solvents can be used to dilute the dispersion until it is within the above viscosity range.

In another embodiment, the second organic liquid is selected from N,N'-dimethyl acetamide, N,N'-dimethylformamide or N-methyl pyrrolidone and the polymer is dissolved therewithin at a concentration in the range of 10 to 30% by weight, preferably 15 to 25% by weight. When the second organic liquid is a liquid polymer, to achieve miscibility with the first organic liquid, the liquid polymer is dissolved in the first organic liquid when they are combined. In one embodiment, the first organic liquid and the second organic liquid are the same. In one embodiment, the first and second organic liquids are dimethyl acetamide (DMAc).

In one embodiment a dianhydride corresponding to the dianhydride moiety in the polyamic acid SMhBN/polyamic acid dispersions, increasing the molecular weight of the imidized polymer may be desired to improve the mechanical properties of the film. A suitable method is to add the corresponding dianhydride (part of polyamic acid) in 10 to 25 milligram quantities, stir the dispersion for ten minutes until the anhydride completely dissolved in the dispersion and measure the viscosity of the dispersion. The addition of the anhydrides in small quantities, mixing the dispersion and measuring the viscosity of the dispersion shall be continued until a dispersion having viscosity in the range 60,000 to 150,000 cp and preferably a viscosity in the range 75,000 to 100,000 cp is achieved. These viscosities are generally associated with polyamic acid solutions that are suitable for solution casting of films followed by imidization to tough, strong polyimide films.

In the case of SMhBN/epoxy dispersions, it is preferable to have a total solid content in the range 40 to 80% by weight, preferably in the range 50 to 70% by weight. Also, it is preferable to have the viscosity of the dispersion in the range 100 to 2000 cp, preferably in the range 200 to 1500 cp.

The composite can be shaped into an article such as a film or sheet, a rod or other stock shape, followed by curing, imidization or other method for effecting the transition from a flowable or formable composite to a non-flowable, non-formable composite. Depending upon the specific features and components of the uncured composite, it may be desirable to extract at least a portion of the organic liquid in order to get a suitably formable composite. Extraction may be effected by any convenient method including but not limited to, heating in a vacuum oven or air circulating oven, or evaporation by casting on a heated drum.

In one embodiment, the second organic liquid is a liquid polymer, and only the first organic liquid is subject to extraction. In one embodiment the second organic liquid is a solvent for a polymer solution, and is also subject to extraction.

In another aspect, the invention provides a film having a thickness of less than 500 μm comprising a polymer and a plurality of surface-modified hexagonal boron nitride particles dispersed therewithin, wherein the surface modified boron nitride particle comprises a hexagonal boron nitride particle having a surface and a substituted phenyl radical bonded to the surface, the substituted phenyl radical being represented by the structure:

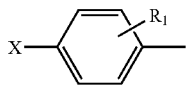

where X is a radical selected from $NH_2$—, HO—, $R^2OC(O)$—, $R^2C(O)O$—, $HSO_3$—, $NH_2CO$—, halogens, alkyl or aryl, including substituted aryl; where $R^1$ is alkyl or alkoxy, and $R^2$ is hydrogen, alkyl or aryl, including substituted aryl.

In one embodiment, $R^1$ is hydrogen. In another embodiment, X is $NH_2$— or HO—. In another embodiment, X is $NH_2$—. In another embodiment, X is HO—.

In one embodiment, the polymer comprises polyamic acid. In a further embodiment, the polyamic acid is in solution. In another embodiment, the polymer is a polyimide. In another embodiment, the polymer is an epoxy-containing polymer either in the liquid state or in solution. In another embodiment, the polymer is a cured epoxy resin.

In one embodiment, the polymer composition comprises 30-70% by weight of the SMhBN. In a further embodiment, the polymer composition comprises 40-65% by weight of the SMhBN. In one embodiment, the average equivalent spherical diameter of the SMhBN in the polymer is in the range of 0.5 μm to 50 μm. In a further embodiment, the average equivalent spherical diameter of the SMhBN in the polymer is in the range of 0.5 to 25 μm. In one embodiment, the SMhBN dispered in the polymer can be characterized by a plurality of particle size distribution peaks characteristic of a so-called multi-modal particle size distribution.

In one embodiment, the film further comprises an organic liquid. In one embodiment the film is formable. In an alternative embodiment the film is non-formable. In general, the formable film is a precursor to the non-formable film. In one embodiment, the formable film is first formed and then, in a single continuous process, converted into the non-formable film. In an alternative embodiment, the formable film is prepared as, for example, roll stock. The roll stock is transferred to a fabricator who forms the formable film into a complex shape, and then causes it to be cured or imidized to the non-formable state while holding the complex shape.

In a further aspect, the present invention provides a process comprising casting onto a surface a dispersion of a plurality of surface modified hexagonal boron nitride particles in a solution of a polymer in a solvent, forming the thus cast dispersion into a viscous liquid film, and, extracting the solvent to form a film having a thickness of less than 500 μm; wherein the surface modified hexagonal boron nitride particles comprise hexagonal boron nitride particles having a surface and a substituted phenyl radical bonded to the surface, the substituted phenyl radical being represented by the structure:

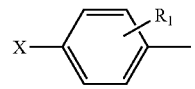

where X is a radical selected from $NH_2$—, HO—, $R^2OC(O)$—, $R^2C(O)O$—, $HSO_3$—, $NH_2CO$—, halogens, alkyl and aryl, including substituted aryl; $R^1$ is alkyl or alkoxy, and $R^2$ is hydrogen, alkyl or aryl, including substituted aryl.

In one embodiment, $R^1$ is hydrogen. In another embodiment, X is $NH_2$— or HO—. In another embodiment, X is $NH_2$—. In another embodiment, X is HO—.

The term "casting" refers to the process by which a polymeric composition is applied to a surface to form a film. Suitable casting processes include but are not limited to adjustable micrometer film applicator (doctor blade), wire wound metering rod (Meyer rod) or slot die, which is commonly used in large scale production.

A composition suitable for film casting ("casting composition") comprises an organic liquid, a polymer dissolved therewithin, and a plurality of SMhBN particles dispersed therewithin. In one embodiment, the casting composition comprises a polymer composite comprising a mixture of a first organic liquid, a second organic liquid miscible in the first organic liquid, a polymer dissolved in at least the first or the second organic liquid, and a plurality of SMhBN particles dispersed therewithin. In one embodiment the polymer is a polyamic acid. In an alternative embodiment, the polymer is an uncured epoxide polymer.

In a further embodiment, the first and second organic liquids are the same. In a still further embodiment, the first and second organic liquids are DMAc. In an alternative embodiment, the casting composition comprises a polymer composite comprising a mixture of a liquid polymer and a first organic liquid miscible in the liquid polymer, and a plurality of SMhBN particles dispersed therewithin. In a further embodiment, the first organic liquid is DMAc. In a still further embodiment, the liquid polymer is a liquid epoxide polymer.

In one embodiment, the surface upon which the casting composition is cast is selected to provide adhering contact with the cast film after solvent extraction and curing or imidizing, thereby resulting in a multi-layer laminate of which at least one layer comprises the cured or imidized film. In one embodiment, the casting composition comprises a polyamic acid and a suitable surface is a polyimide. In a further embodiment, the casting composition comprises an epoxy resin and a suitable surface is a cured epoxy. In another embodiment the surface is a that of a metal foil. In a further embodiment, the metal foil is copper foil.

When casting the film on a metal foil, the metal surface can be roughened to achieve adhesion. In one embodiment, casting is effected onto the matte side of an electrodeposited copper foil. In an alternative embodiment, casting is effected onto the shiny surface of an electrodeposited copper foil, and the foil acts as a release layer. If casting is effected onto the matte surface but the polymer is not fully cured or imidized, it may still be possible to separate the two layers by ordinary methods. However, if the polymer is fully cured or imidized, the layers are tightly bound.

Other materials suitable for use as release layers include but are not limited to polyethylene, polyvinyl chloride, polyethylene terephthalate, polyethylene naphthalate, and polycarbonate.

The quality of the films so-cast depends on the uniformity of the dispersion in the coating composition, absence of trapped air bubbles, the viscosity of the dispersion, the accuracy in metering of the casting composition to produce uniform thickness, etc. The uniformity of the casting composition depends in part on achieving wetting of the particles by the solvent and the resin, in part on particle size and agglomeration. It is preferable to disperse the particles using a high shear mixture in a moderately viscous resin solution. The particles tend to settle during storage of a dispersion in a low viscosity polymer solution. A suitable epoxy coating composition has a viscosity in the range 100-2000 cp. A suitable polyamic acid coating composition has a viscosity in the range of 75000-100000 cp. Air bubbles can be removed by stirring under vacuum.

In a further aspect, the present invention provides a process comprising disposing an electrically conductive metallic layer upon the surface of a polymer composite film less than 500 µm in thickness, having a surface, followed by the application of pressure or a combination of pressure and heat to effect bonding therebetween, the polymer composite film comprising a polymer and a plurality of surface-modified hexagonal boron nitride particles dispersed therewithin comprising hexagonal boron nitride particles having a surface and a substituted phenyl radical bonded to the surface, the substituted phenyl radical being represented by the structure:

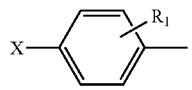

where X is a radical selected from $NH_2$—, HO—, $R_2OC(O)$—, $R_2C(O)O$—, $HSO_3$—, $NH_2CO$—, halogens, alkyl or aryl, including substituted aryl; where $R_1$ is alkyl or alkoxy, and $R_2$ is hydrogen, alkyl or aryl, including substituted aryl.

In one embodiment, $R_1$ is hydrogen. In another embodiment, X is $NH_2$— or HO—. In another embodiment, X is $NH_2$—. In another embodiment, X is HO—.

In one embodiment the metal is copper. In a further embodiment the copper is in the form of a copper foil. In one embodiment, the conductive metal layer is in the form of conductive pathways.

In one embodiment the process further comprises disposing an adhesive layer between the polymeric composite film and the conductive metal layer.

Other suitable conductive metal layers suitable include, but are not limited to stainless steel, copper alloys, aluminum, gold, silver, tungsten, nickel, and alloys thereof.

Suitable materials for use in the adhesive layer include but are not limited to epoxies, acrylics, phenolic, thermoplastic polyimides, poly-etherimides, polyester, polyamide, polyamide-imides, polyimide, polyetherimides, polyether-ketones, polyether-sulfones and liquid crystal polymers.

In a further aspect, the invention provides a multi-layer article comprising a layer of an electrically conductive metal adheringly contacting the surface of a polymeric composite film less than 500 µm in thickness, having a surface, the polymeric composite film comprising a polymer and a plurality of surface-modified hexagonal boron nitride particles dispersed therewithin comprising hexagonal boron nitride particles having a surface and a substituted phenyl radical bonded to the surface, the substituted phenyl radical being represented by the structure:

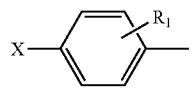

where X is a radical selected from $NH_2$—, HO—, $R^2OC(O)$—, $R^2C(O)O$—, $HSO_3$—, $NH_2CO$—, halogens, alkyl and aryl, including substituted aryl; $R_1$ is alkyl or alkoxy, and $R^2$ is hydrogen, alkyl or aryl, including substituted aryl.

In one embodiment, $R^1$ is hydrogen. In another embodiment, X is $NH_2$— or HO—. In another embodiment, X is $NH_2$—. In another embodiment, X is HO—.

In one embodiment the metal is copper. In a further embodiment the copper is in the form of a copper foil. In one embodiment, the conductive metal layer is in the form of conductive pathways. In one embodiment the multi-layer article further comprises an adhesive layer between the polymeric composite film and the conductive metal layer.

The metal layers can be formed of any metal, including copper, gold, silver, tungsten or aluminum. In one embodiment, the metal layer is a copper foil. The copper foil can be created in any manner known in the art including electro deposition or rolled copper foil.

In one embodiment, the adhesive layer comprises a thermoplastic polymer. Suitable thermoplastic polymers include but are not limited to polyimides made by reacting aromatic di-anhydrides with aliphatic diamines. Other materials useful as a dielectric adhesive layer include polyester, polyamide, polyamide-imides, polyetherimides, polyether-ketones, polyether-sulfones and liquid crystal polymers. In an alternative embodiment, the adhesive layer comprises a thermoset polymer. Suitable thermoset polymers include but are not limited to epoxies, phenolic resins, melamine resins, acrylic resins, cyanate resins, and combinations thereof. Generally, the adhesive layer has a thickness in the range of 3 to 35 µm, and has an in-plane coefficient of thermal expansion (CTE) of 25 to 90 ppm/° C. at 20° C.

In one embodiment, the adhesive layer comprises a polyimide with glass transition temperatures of 150 to 350° C. Generally, bonding temperatures are 20 to 50 degrees higher than the glass transition temperature. In a further embodiment, the adhesive polyimide is synthesized by condensing an aromatic dianhydride with a diamine component comprising 50 to 90 mol-% aliphatic diamine and 1 to 50 mol-% aromatic diamine. In a further embodiment, the aliphatic diamine is hexamethylene diamine (HMD) and the aromatic diamine is 1,3-bis-(4-aminophenoxy)benzene, the aromatic dianhydride is a combination of 3,3',4,4'-benzophenone tetracarboxylicdianhydride (BTDA) and 3,3',4,4'-biphenyl tetracarboxylic polymer having a glass transition temperature in the range of 150 to 200° C.

In an another embodiment, the adhesive is a heat-sealable copolyimide comprising from 60 to 98 mole % of repeating imide units of the formula I

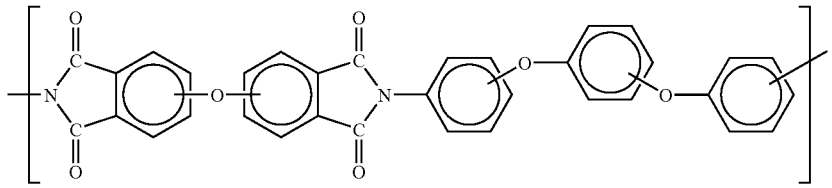

and from 2 to 40 mole % of other repeating imide units of the formula II

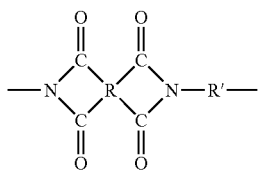

wherein R is the radical of a tetravalent organic carboxylic dianhydride selected from the group consisting of pyromellitic dianhydride, 4,4'-oxydiphthalicdianhydride, 3,3',4,4'-benzophenone tetra-carboxylic dianhydride, 2,2',3,3'-benzophenone tetracarboxylicdianhydride, 3,3',4,4'-biphenyl tetracarboxylicdianhydride, 2,2',3,3'-biphenyl tetracarboxylicdianhydride, 2,2-bis(3,4-dicarboxyphenyl)hexafluoropropane dianhydride, bis(3,4-dicarboxyphenyl)sulfone dianhydride and m-phenylene bis(trimellitate)dianhydride; and wherein R' is the radical of a divalent aromatic or aliphatic diamine selected from the group consisting of p-phenylenediamine, hexamethylene diamine, heptamethylene diamine, octamethylene diamine, 4,4'diaminodiphenylether, 3,4'-diaminodiphenylether, 1,3-bis(4-aminophenoxy)benzene, 1,2-bis(4aminophenoxy)benzene, 1,3-bis(4-aminobenzoyloxy)benzene, 4,4'-diaminobenzanilide, 4,4'-bis(4-aminophenoxy)phenyl ether and a polysiloxanediamine, provided that the repeating imide units of formula (I) are different from the repeating imide units of formula (II).

The conductive metal layer thickness can generally be in the range of 2 to 500 μm, and in one embodiment, the conductive metal layer thickness is in the range of 3 to 35 μm. In one embodiment, the conductive metal layer is a copper foil having a CTE in a range between 15 and 17 ppm/° C. at 20° C.

The conductive layer can be pre-treated mechanically or chemically to improve laminate adhesion. Pretreatments commonly practiced in the art include but are not limited to electro-deposition; immersion-deposition along the bonding surface of a thin layer of copper, zinc, chrome, tin, nickel, cobalt, other metals, and alloys of these metals. Apart from roughening the surface, chemical pretreatment may also lead to the formation of metal oxide groups, enabling improved adhesion between the metal layer and dielectric multilayer. In one embodiment, the pretreatment is applied to both sides of the metal, enabling enhanced adhesion for both sides of the metal.

In one embodiment, a resin-coated foil is prepared by coating a metallic, preferably copper, foil with a casting composition described supra. In one embodiment, the casting composition is metered onto a moving copper foil using a combination of coating and compression rolls in a continuous process. Other suitable coating processes are blade or knife coating, slot or extrusion coating, gravure coating, slide coating, and curtain coating. In one embodiment, the coated foil is dried, typically in an oven, to increase the viscosity of the uncured coating, partially curing or imidizing it to form a so-called B-stage composition. In one embodiment, the process is a continuous coating process, and the foil coated with the B-stage composition can be wound on a roll for further use. In some embodiments, a first coating layer is fully cured, and then the coated foil is further coated with one or more additional layers.

In one embodiment, the conductive metal layer is formed on the surface of the film, by dry plating or wet plating. Dry plating methods known in the art include sputtering or ion plating. In wet plating, the surface of the cured layer is first roughened with an oxidizing agent such as a permanganate, a bichromate, ozone, hydrogen peroxide/sulfuric acid or nitric acid to form an uneven surface ("anchor") for anchoring the conductive layer. The conductor can then be formed by a method combining electroless plating and electroplating.

The multi-layer laminate however formed can serve as the starting material in the production of a printed circuit board. Printed circuit boards are prepared by the application of photoresist material to the metallic surface. In the case of a positive photoresist, the pattern of a circuit is photoimaged onto the surface of the photoresist, thereby photopolymerizing the positive photoresist. Photoimaging can involve coherent and/or non-coherent light sources. One method for photoimaging is through a phase mask. The pattern of photopolymerization replicates the circuit to be formed. Following photoimaging, the resin-coated foil is subject to a solvent that dissolves the unpolymerized photopolymer. The thus treated resin-coated foil is then subject to chemical treatment of the exposed metal. After the exposed metal has been removed chemically, the resin-coated foil is then subject to etching, such as ion-beam etching, to remove the layer of photopolymerized material, thereby exposing the pattern of conductive pathways beneath, making a printed circuit board that is now ready to receive electronic components. The printed circuit board so formed can serve as the core layer of a multi-layer printed circuit board as described supra, or it can remain a single layer printed circuit board. Depending upon the thickness of the coating prepared from the coating composition, and the nature of the cured or imidized polymer thereof, the printed circuit board can be rigid or flexible.

In a further embodiment, the cured or imidized layer can be bored with a drill, a laser or the like to form via holes or through-holes.

EXAMPLES

Measurements

The glass transition temperature ($T_g$) and the in-plane thermal expansion coefficient (CTE) of the cured film was determined using a Thermal Mechanical Analyzer by following IPC test method Number 2.4.24.5. CTE was determined in a single direction in the plane of the film. The glass transition, modulus and loss modulus of the film was determined using a Dynamic Mechanical Analyzer by following IPC test method Number 2.4.24.4.

The heat conductivity in a direction normal to the plane of the film was calculated using this relationship:

Conductivity=Diffusivity×$C_p$×Bulk density.

The specific heat ($C_p$) of the film was measured using differential scanning calorimetry (DSC) against a sapphire standard using standard methods. Values of thickness t and bulk density ρ (w/{π$r^2$·t}) are based on room temperature measurements.

The thermal diffusivity was measured at 25° C. using a Netzsch LFA 447 NanoFlash® Xenon Flash Apparatus, available from NETZSCH-Gerätebau GmbH, Selb, Germany. Each 1 inch diameter (25.4 mm) die-cut specimen was sputter-coated with a layer of gold on both sides, followed by spraying on a layer of graphite. The specimen so prepared was mounted in a holder cooled by a circulating bath to maintain specimen temperature constant during the measurement. Flashlamp gain was set at 1260 in a range from 78 to 5000. Pulse widths of 10 and 66 ms were employed. The detector was a liquid nitrogen cooled IR detector. Each data point represents the average of four specimens.

Example 1 and Comparative Example A 8.0 g of para-phenylene diamine was dissolved in 100 ml of deionized water and 57 ml of 0.5M hydrochloric acid at room temperature. 5.1 g of sodium nitrite dissolved in 50 ml of deionized water was added to the solution to make the corresponding diazonium chloride. The diazonium salt solution was added to a dispersion containing 25 g of hBN (NX1 grade, Momentive Performance Materials, Strongsville, USA) dispersed in 200 ml of methanol and 800 ml of water. 6.0 g gram of iron powder (325 mesh) was added to this dispersion and stirred at room temperature. After five minutes, 250 ml of 0.5 M hydrochloric acid was added to this dispersion and stirred for an additional 30 minutes (min). The dispersion was filtered, washed with water, ammonia solution (25 cc of ammonia solution in one liter of water) and then with methanol. The product was dried at 100° C. overnight in a vacuum oven to produce dry SMhBN.

Thermogravimetric analysis (TGA—10° C./min heating rate, air atmosphere) showed that the specimen so prepared contained 2.55 weight-% (wt-%)) of aminophenyl groups on the basis of the weight of the SMhBN based on weight loss between 250° C. to 600° C. Time of Flight-Secondary Ion Mass Spectroscopy (ToF-SIMS) analysis of the SMhBN showed positive ion peaks at m/z 92 and 106. The positive ion peak at m/z at 92 confirmed the presence of —$C_6H_4$—$NH_2$ groups on the surface of the hBN. The m/z ion peak at 106 corresponded to the structure —N—C6H4-NH2, confirming that the aminophenyl group was attached to the N atom in the hBN through a covalent bond.

Figure 2A:
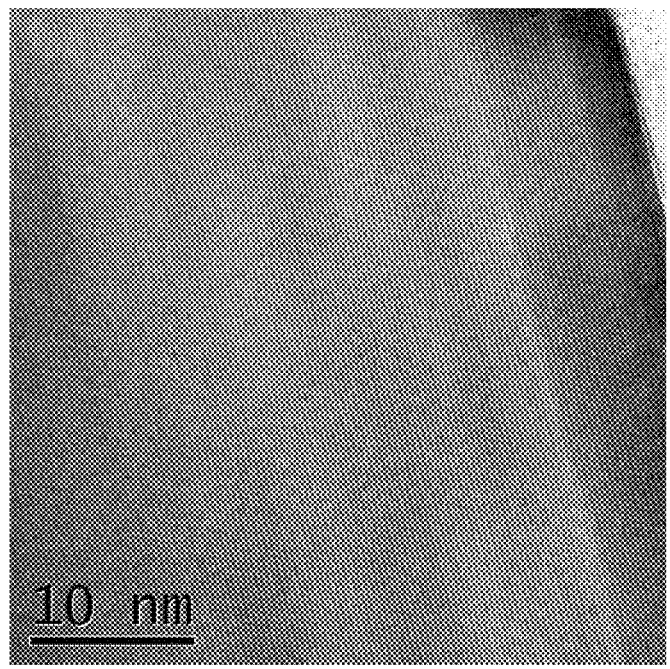
FIG. 2a is a transmission electron micrograph (TEM) of the platelet edges of hBN as received (Comparative Example A).
Figure 2B:
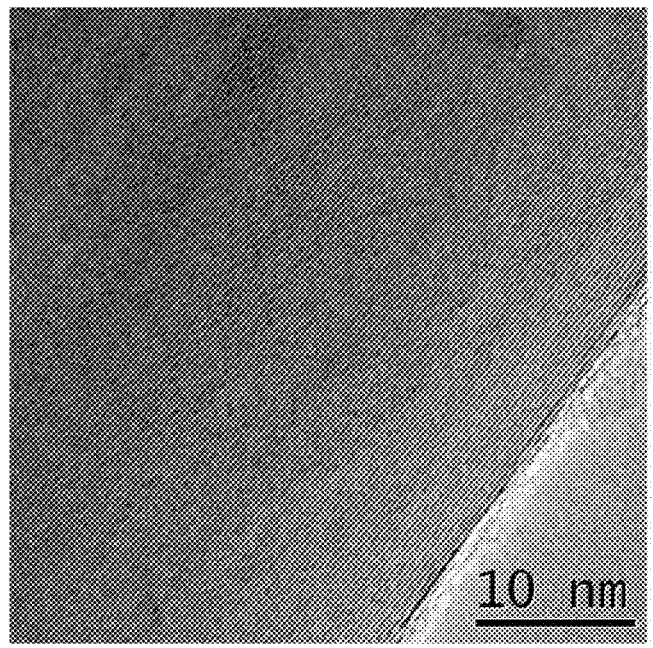
FIG. 2b is a TEM of the platelet edges of the SMhBN prepared according to Example 1.

FIG. 2a is a transmission electron micrograph (TEM) of the platelet edges of hBN as received (Comparative Example A). FIG. 2b is a TEM of the platelet edges of the SMhBN prepared according to Example 1. The virtually identical appearance of the two samples indicated little or no intercalation of the aminophenyl radical between the platelets of hBN. FIGS. 1a and 1b show a 'd' (0002) spacing of 3.55 Å and 3.46 Å respectively.

Figure 3A:
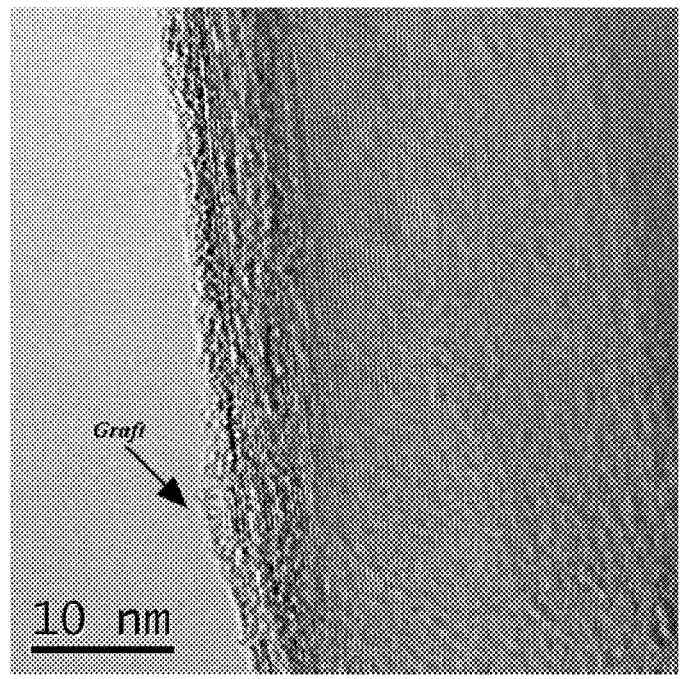
FIG. 3a. is a TEM of the basal plane in the SMhBN of Example 1, a view from the platelet edges.
Figure 3B:
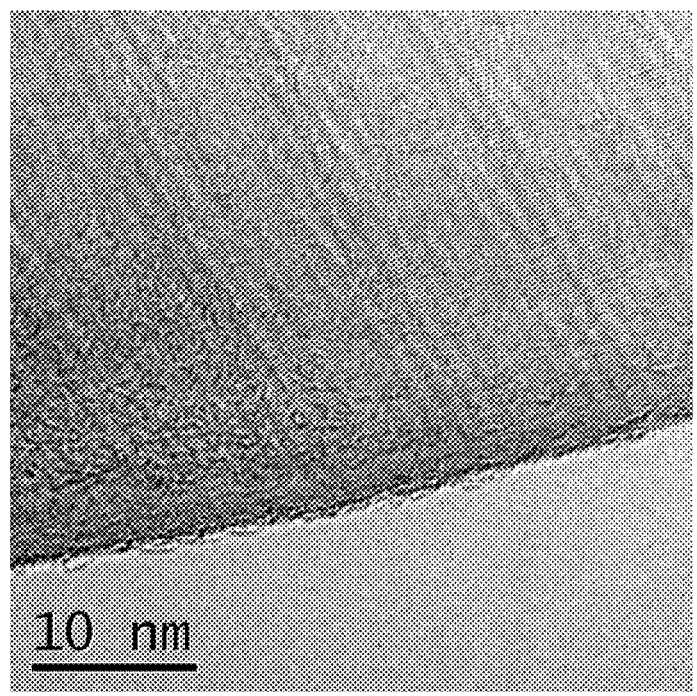
FIG. 3b is a TEM of the platelet edges in the SMhBN of Example 1, a view from the basal plane.

FIG. 3a. is a TEM of the basal plane in the SMhBN of Example 1, a view from the platelet edges. FIG. 3b is a TEM of the platelet edges in the SMhBN of Example 1, a view from the basal plane. FIGS. 3a and 3b showed an amorphous coating on the basal plane and none on the edges, thus showing that the surface modification took place only on the basal plane.

Examples 2-5

The procedures of Example 1 were followed but the amount of para-phenylene diamine (PPD) was varied. The amounts of sodium nitrite, the hydrochloric acid and the iron were changed proportionately with para-phenylene diamine on a molar basis. The weight loss data measured from TGA (between 250-600° C.) was taken as the amount of aminophenyl grafting on the hBN surface. Results are shown in Table 2

TABLE 2

| Example | Reactant Amount | | | Amount of aminophenyl grafting on the hBN surface (wt. %) |
|---|---|---|---|---|
| | PPD (g) | Na(NO$_2$) (g) | Fe (g) | |
| 2 | 1.0 | 0.638 | 0.75 | 0.38 |
| 3 | 2.0 | 1.275 | 1.5 | 1.02 |
| 4 | 4.0 | 2.55 | 3.0 | 1.93 |
| 5 | 8.0 | 5.10 | 6.0 | 2.55 |

Examples 6-8

The procedure of Example 1 was used to surface modify different grades of hBN. 4.0 g of PPD was dissolved in 50 ml of deionized water and 28.5 ml of 0.5 M hydrochloric acid at room temperature. 2.55 g of sodium nitrite dissolved in 50 ml of deionized water was added to this solution to make the corresponding diazonium chloride. This diazonium salt solution was added to dispersions each containing 25 g of a grade of hexagonal boron nitride (NX1, PT120 & PT620, Momentive Performance Materials, Strongsville, USA) in 100 ml of methanol and 400 ml of water. 3.0 g gram of iron powder (325 mesh) was added to each dispersion and stirred at room temperature. After five minutes, 125 ml of 0.5 M hydrochloric acid was added to each dispersion and stirred for additional 30 min. Each dispersion was filtered, washed with water, ammonia solution consisting of 25 cc of ammonium hydroxide in one liter of water, then with methanol and dried at 100° C. in a vacuum oven. The amount of surface functional group was determined by thermogravimetric analysis. Results are shown in Table 3

TABLE 3

| Example | hBN grade | particle size* (μm) | surface area* (m$^2$/g) | Amount of surface grafted (%) |
|---|---|---|---|---|
| 6 | NX1 | 0.7 | 20.0 | 1.93 |
| 7 | PT120 | 12-13 | 2.0 | 0.42 |
| 8 | PT620 | 16.0 | 4.4 | 0.52 |

*supplier data

Example 9

This same procedure reported in Example 1 was also used to make hydroxyphenyl grafting on an hBN surface. The PPD was replaced with the same amount of para-amino phenol. After reaction, TGA showed that the SMhBN thus prepared contained about 0.51% by weight of hydroxy phenyl groups on the basis of the total weight of SMhBN. TOF-SIMS analysis of the SMhBN, showed positive ion peaks at m/z 93 and 107. The positive ion peak at 93 confirmed —$C_6H_4$—OH groups on the surface of the hBN. The peak at 107 corresponded to —N—C6H4-OH, confirming that the hydroxyphenyl group was attached to the N atom in the hBN through a covalent bond.

Example 10 and Comparative Example B

A polyamic acid solution was formed, by reacting 1.0 mole of 1,3-(4-aminophenoxy)benzene (134APB) with 0.8 mole of 4,4'-oxy-3,4,3',4'-diphthalic anhydride (ODPA) and 0.2 mole of pyromellitic dianhydride (PMDA) in dimethyl acetamide (DMAc) solvent at room temperature under a nitrogen atmosphere. The viscosity of the polyamic acid solution so prepared was 8500 cp at 1.40 s−1 shear rate; the solids content was 19.5% by weight.

Comparative Example B 40.0 g of the above polyamic acid solution was mixed with 7.8 g of the as received hBN and the dispersion was stirred at room temperature for 30 minutes. The viscosity of the dispersion was measured using a Brookfield Model DV-II+ Viscometer. Results are shown in Table 4. This composition corresponded to that of a cured film containing 50% resin and 50% hBN by weight.

Example 10

A similar dispersion to that of Comparative Example B was made using the same amounts of the polyamic acid, the SMhBN of Example 1, and the viscosity was measured. The data is summarized in Table 4.

TABLE 4

| | Viscosity (cp) | |
|---|---|---|
| Shear rate (1/s) | Comparative Example B | Example 10 |
| 1.40 | 36000 | 28700 |
| 1.12 | 42120 | 30000 |
| 0.70 | 52200 | 32000 |

Example 11

30 g of SMhBN prepared as in Example 1 was combined with 60 g of DMAc using a mechanical stirrer to form a dispersion. 51.3 g of the polyamic acid solution of Example 10 was added to the SMhBN dispersion and mixed thoroughly using a Silverson Homogenizer for four minutes at 75% speed to form a SMhBN/polyamic acid concentrate or masterbatch.

56.51 g of the thus made SMhBN/polyamic acid masterbatch was mixed with an additional 29.84 g of the polyamic acid solution using a mechanical stirrer for about 20 min to make a SMhBN/polyamic acid dispersion/solution that corresponded to a concentration of 55% by weight of SMhBN in the cured film. 25 mg aliquots of ODPA were added to the SMhBN/polyamic acid dispersion/solution. After each addition, the dispersion/solution was mixed for about ten minutes until the solids dissolved completely. After a total of six aliquots of ODPA, the viscosity of the dispersion/solution had increased to 77400 cp at 0.70 s$^{-1}$ shear rate. The thus prepared dispersion/solution was kept in a desiccator under vacuum for 30 minutes to remove the trapped air bubbles The resulting dispersion/solution was cast onto the surface of a polyester film using a doctor blade with a 0.010 inch (in) opening to make a film 12" in length and 8" in width. The two layer film thus formed was baked at 80° C. for thirty minutes in an air circulating oven. The two layers were separated, and the SMhBN/polyamic acid film was clamped into place in a metal frame and baked at 100° C. in an air circulating oven for fifteen minutes. The B-stage film so produced was then cured in a furnace by heating at 5° C./min to 300° C., holding at 300° C. for five minutes; then rapidly heated to 375° C. and held at 375° C. for five minutes. At the end of the five minute soak, the furnace was turned off and the thus treated specimen was allowed to cool, still in the furnace, to room temperature.

Comparative Example C

The hBN concentrate was made by mixing 60 g of DMAc and 30 g of the as-received hBN (NX1 grade) using a mechanical stirrer. Then 51.3 g of the polyamic acid solution described in Example 10 was added to this dispersion and mixed thoroughly using a high shear Silverson Homogenizer for four minutes at 75% speed. 56.51 g of the thus made hBN concentrate was mixed with 29.84 g of the polyamic acid solution using a mechanical stirrer for about 20 min to make a dispersion/solution of polyamic acid containing 55% by weight of hBN in the cured film. ODPA in 25 milligram aliquots was added to the so-prepared dispersion/solution, and mixed for about ten minutes for each aliquot, until the solids dissolved completely in the dispersion. A total of two such aliquots of ODPA were added to the dispersion/solution such that the viscosity of the dispersion/solution increased to 79200 cp at 0.70 s−1 shear rate. The resulting dispersion/solution was de-gassed, cast into a film, and post-treated in the manner described for the dispersion/solution of Example 11.

A control polyimide film was made using the polyamic acid solution of Example 10. 100 g of the polyamic acid solution was mixed with 100 mg of ODPA using a mechanical stirrer for about 10 min until all the solids dissolved. The viscosity of the thus prepared polymer solution was 72200 cp at 0.70 s−1. The same procedure reported in Example 11 was used to make and cure a film.

Thermal and mechanical properties of the films produced in Example 11, Comparative Example C, and the unfilled polyimide film were determined using both Thermal Mechanical Analysis and Dynamic Mechanical Analysis. The results are shown in Table 5

TABLE 5

| Comparison of Polyimide Films | | | |
|---|---|---|---|
| | Polyimide Film | Example 11 | Comp. Ex. C |
| $T_g$ (° C.)* | 244 | 244 | 244 |
| CTE (ppm/° C.): | | | |
| 25-200° C. | 62 | 24 | 31 |
| 250-290° C. | 2806 | 112 | 215 |
| $T_g$ (° C.)** | 236 | 241 | 236 |

TABLE 5-continued

Comparison of Polyimide Films

| Polyimide Film | Example 11 | Comp. Ex. C |
|---|---|---|
| Modulus at 25° C. (GPa) | 3.522 | 10.63 | 11.16 |
| Modulus at 500° C. | Film broke at 415° C. | 1.97 | 0.87 |

*Determined by TMA.
**Determined by DMA.

Examples 12-14. and Comparative Example D

The SMhBN of Example 1 was combined with polyamic acid solution and converted to polyimide films as described in Example 1, but in different relative proportions, as indicated in Table 6. Table 6 shows the CTE of the films so-prepared.

TABLE 6

| | Film Composition | | CTE (ppm/° C.) | |
|---|---|---|---|---|
| | SMhBN(%) | Polyimide (%) | 50-225° C. | 260-300° C. |
| Comp. Ex. D | — | 100 | 62 | 2806 |
| Ex. 12 | 40 | 60 | 34 | 141 |
| Ex. 11 | 55 | 45 | 24 | 112 |
| Ex. 13 | 60 | 40 | 18 | 69 |
| Ex. 14 | 65 | 35 | 14 | 52 |

Examples 15-22 and Comparative Example D

The SMhBN samples prepared in Examples 6-8 were combined over a range of proportions with polyamic acid following the procedures in Example 11 to produce the SMhBN/polyimide composite films listed in Table 7. Thermal conductivity normal to the plane of the films was determined and the results also given in the table 7.

TABLE 7

| | Film composition | | |
|---|---|---|---|
| | Aminophenyl grafted hBN (wt. %) | Polyimide (wt. %) | Thermal conductivity (W/m · ° K) |
| Comp. Ex. D | 0 | 100 | 0.209 |
| Ex. 15 | 55 NX1 | 45 | 1.130 |
| Ex. 16 | 60 NX1 | 40 | 1.128 |
| Ex. 17 | 65 NX1 | 35 | 1.356 |
| Ex. 18 | 50 PT620 | 50 | 0.993 |
| Ex. 19 | 25 NX1 + 25 PT120 | 50 | 1.033 |
| Ex. 20 | 30 NX1 + 30 PT120 | 40 | 1.292 |
| Ex. 21 | 25 PT120 + 25 PT620 | 50 | 1.377 |
| Ex. 22 | 30 PT120 + 30 PT620 | 40 | 2.219 |

Example 23

24.8 g of ODPA, was combined with 4.25 g PMDA to form a mixture. The mixture so formed was added slowly over a period of two hours to a solution of 29.2 g of 1,3-(4-aminophenoxy)benzene (134APB) in 350 ml DMAc to form a 15% polyamic acid solution. After a viscosity of 10000 cp was reached, 11 g of the SMhBN of Example 1, was added and stirred well to get a fine dispersion. Then, the viscosity of the polymer was raised to 75000 centipoise by slowly adding a small amount of PMDA with continuous stirring.

The solution mixture was then degassed under vacuum and cast as a film on a glass plate to make about 12×12" size film. The thus coated plate was dried for 15 min on a hot plate set at 100° C. The film was removed from the hot plate and cooled to room temperature. The film was mounted on a pin frame. The thus mounted film was dried and cured in an oven programmed to increase in temperature from 120 to 300° C. over an hour. Then the frame-mounted film was removed from the oven and immediately placed in a second oven that had been preheated to 400° C. The frame-mounted film was heated in the second oven for five minutes, and then removed, and cooled on the bench.

The cooled film was removed from the frame, and the edge trimmed to get an 8×10 in specimen. The so-trimmed film was then placed between two 12×12 in (18 um thick) copper foils. The package so formed was then inserted into a larger sandwich consisting of a caulk plate/aluminum foil, Teflon® PFA sheet/copper foil/SMhBN-polyimide composite film/copper foil/Teflon® PFA sheet/aluminum foil/caulk plate. The multi layer sandwich so formed was placed between the platens of a hydraulic press set at a temperature of 150° C. within a vacuum oven. The press was then heated to 350° C. and a pressure of 350 psi was applied to the platens. The press was cooled to 150° C. and the package was removed from the press and the laminate removed.

Example 24 and Comparative Examples E and F

An epoxy resin composition was prepared by dissolving in 25 ml of methyl ethyl ketone 9.0 g of poly(o-cresyl glycidyl ether)-co-formaldehyde, (molecular weight 1080, Aldrich, USA), 0.9 g of PKHH phenoxy resin (Phenoxy Specialties, Rock Hill, S.C., USA), 0.9 g of bishenol A, 3.6 g of Durite® D_SD-1819, a dicyclopentadiene-phenol adduct (Borden Chemical Inc., Louisville, Ky.) and 0.86 g of 2-ethyl-4-methyl imidazole. The thus formed epoxy solution was stirred using a magnetic stirrer at room temperature for 30 min.

14.4 g of the hydroxyphenyl grafted SMhBN of Example 9 was added to the above-prepared epoxy solution and the resulting mixture was stirred at room temperature followed by agitation using an ultrasonic probe (Dukane Sonic Welder equipped with a 1watt head and ¼" sonic horn) for four minutes. The dispersion so produced was degassed under vacuum. The thus sonicated dispersion was cast onto a polyester film using a doctor blade set with a 0.010 in. opening. The cast film was dried in an air circulating oven at 50° C. for thirty minutes, peeled off the film from the base polyester film. The dried film was placed on a porous fiberglass/Teflon sheet, cured in an air circulating oven by heating at 130° C. for thirty minutes, at 150° C. for ten minutes and at 170° C. for one hour.

Comparative Example E

A film identical to that of Example 24 was prepared except that the NX1 hBN was used as received.

Comparative Example F

And additional film was prepared in the same manner, but without any hBN.

Table 8 shows CTE results of the three films.

| CTE (ppm/° C.) | Comp. Ex. F | Ex. 16 | Comp. Ex. E |
|---|---|---|---|
| 25-150° C. | 79 | 27 | 28 |
| 170-240° C. | 156 | 56 | 66 |

I claim:

1. A composition comprising hexagonal boron nitride particles having a surface and a substituted phenyl radical bonded to the surface, the substituted phenyl radical being represented by the structure:

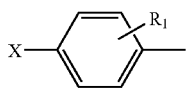

wherein X is a radical selected from $NH_2$—, HO—, $R^2OC(O)$—, $R^2C(O)O$—, $HSO_3$—, $NH_2CO$—, halogens, alkyl and substituted or unsubstituted aryl; $R^1$ is hydrogen, alkyl or alkoxy, and $R^2$ is hydrogen, alkyl or substituted or unsubstituted aryl.

2. The composition of claim 1 wherein $R^1$ is hydrogen, and X is $NH_2$—.

3. The composition of claim 1 wherein $R^1$ is hydrogen, and X is HO—.

4. The composition of claim 1 further comprising a concentration of 0.1 to 4.0% by weight of substituted phenyl radical bonded to the surface based on the total weight of the composition.

5. A process comprising reacting particles of hexagonal boron nitride (hBN) with a substituted phenyl diazonium chloride in an alcohol/water solution in the presence of metallic iron and HCl to form a reaction product, and recovering the reaction product; wherein the alcohol/water solution has a water concentration of at least 50% by volume; and wherein the substituted phenyl diazonium chloride is represented by the formula

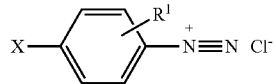

wherein X is a radical selected from $NH_2$—, HO—, $R^2OC(O)$—, $HSO_3$—, $NH_2CO$—, halogens, alkyl, and substituted or unsubstituted aryl; $R^1$ is alkyl or alkoxy, and $R^2$ is hydrogen, alkyl, or substituted or unsubstituted aryl.

6. The process of claim 5 wherein $R^1$ is hydrogen, and X is $NH_2$—.

7. The process of claim 5 wherein $R^1$ is hydrogen, and X is HO—.

8. The process of claim 5 wherein the water concentration is at least 80% by volume.

9. The process of claim 5 wherein the molar ratio of substituted phenyl diazonium chloride to hBN is in the range of 0.005:1 to 0.1:1.

10. The process of claim 5 wherein the iron is added in molar excess with respect to the substituted phenyl diazonium chloride.

* * * * *